United States Patent [19]

Withjack

[11] Patent Number: 4,982,086

[45] Date of Patent: Jan. 1, 1991

[54] METHOD OF POROSITY DETERMINATION IN POROUS MEDIA BY X-RAY COMPUTED TOMOGRAPHY

[75] Inventor: Eric M. Withjack, Plano, Tex.

[73] Assignee: Atlantic Richfield Company, Los Angeles, Calif.

[21] Appl. No.: 219,611

[22] Filed: Jul. 14, 1988

[51] Int. Cl.$^5$ .................... G01V 5/08; G01V 5/12
[52] U.S. Cl. .................... 250/255; 250/258; 250/256; 250/264
[58] Field of Search ............... 250/255, 256, 258, 259, 250/264; 378/5

[56] References Cited

U.S. PATENT DOCUMENTS

| | | | |
|---|---|---|---|
| 4,649,483 | 3/1987 | Dixon, Jr. ............... | 250/256 |
| 4,663,711 | 5/1987 | Vinegar et al. ............ | 378/5 X |
| 4,782,501 | 11/1988 | Dixon, Jr. ............... | 250/253 |

OTHER PUBLICATIONS

Charles W. Finkel, Jr., *Encyclopedia of Applied Geology*, vol. XIII, Van Nostrand Reinhold Co., N.Y., 1984, pp. 281-282 and pp. 526-528.

*Primary Examiner*—Constantine Hannaher
*Assistant Examiner*—Jacob M. Eisenberg
*Attorney, Agent, or Firm*—Michael E. Martin

[57] ABSTRACT

A method for porosity determination in porous media such as earth and rock core samples by x-ray computed tomography in which a sample of the porous medium is scanned after saturation with a first reference fluid and then after saturation with a second reference fluid to determine the linear attenuation coefficients of the sample saturated with the respective fluids. The method includes determining the linear attenuation coefficients of the respective fluids and comparing the difference in the attenuation coefficient of the respective fluids and the attenuation coefficient of the samples as saturated with the fluids to determine the porosity of the porous medium. The respective fluids may be a gas and a liquid wherein the x-ray absorption of the two fluids is significantly different. The fluids may be different liquids or a single gas at different pressure conditions to obtain the different absorption characteristics.

7 Claims, 1 Drawing Sheet

METHOD OF POROSITY DETERMINATION IN POROUS MEDIA BY X-RAY COMPUTED TOMOGRAPHY

BACKGROUND OF THE INVENTION

1. Field of the Invention

The present invention pertains to a method for porosity determination in porous media, such as are encountered in petroleum engineering and related earth science studies, by x-ray computed tomography (CT).

2. Background

X-ray methods such as shadow graph techniques to study oil recovery possibilities in core samples under laboratory conditions are known. Moreover, with the development of computed tomography (CT) a distinct cross-sectional image or "a slice" may be obtained through an object. U.S. Pat. No. 4,663,711 to Vinegar et al describes a method for modeling flooding of a petroleum reservoir using computed tomography wherein x-rays of two different energy levels are applied to a core sample and at least one of the fluids injected in the core sample is doped with a strong photoelectric absorbing material. Multiple scans are conducted at the two energy levels during the displacement process and the resulting data permit calculation of the oil, water, and gas phase saturations of the core. However, it is also important in the development of petroleum resources and other activities to be able to determine the porosity of a porous media, as well as determine the extent of saturation of the media with a certain composition or compositions and the relative permeability of certain media.

SUMMARY OF THE INVENTION

The present invention provides an improved method of determining the porosity of porous media, in particular, samples of earth formations or so called core samples using x-ray computed tomography.

In accordance with an important aspect of the present invention, the porosity of a porous medium is determined by determining the x-ray linear attenuation coefficient, $\mu_{1P}$, of a sample of a porous medium with a single fluid occupying the pore space of the medium. If two attenuation measurements are taken with a different fluid occupying the pore volume or space the equations expressing the linear attenuation coefficient of the porous medium, including the fluid, may be combined to express porosity in terms of the x-ray linear attenuation coefficient of the medium with each of the uniform or single fluids occupying the pore spaces individually and the x-ray linear attenuation coefficients of the respective fluids.

In accordance with another aspect of the present invention, there is provided a method for determining the porosity of a porous medium using x-ray computed tomography for determining the attenuation coefficients wherein a so called CT number is obtained by converting attenuation coefficients into the CT number for the material of interest. The CT number may be calculated from the equation:

$$\text{CT number} = K(\mu - \mu_{water})/\mu_{water} \tag{1}$$

where, for example, $\mu$ is the x-ray linear attenuation coefficient of the material occupying a volume element during an x-ray scan of the material, and $\mu_{water}$ is the x-ray linear attenuation coefficient of a reference material (water) occupying the same element during a calibration scan. The constant K is normally assigned a value of 1,000.

In accordance with yet another aspect of the present invention a method for determining the porosity of a porous medium by x-ray computed tomography scanning is carried out by obtaining a CT number for a first reference fluid, such as air, by scanning a suitable sample holder for the porous medium while said holder is otherwise empty, obtaining a CT number for the porous medium saturated with air by scanning a clear, dry sample of the porous medium, by scanning a second reference fluid which attenuates x-rays to a much greater extent than the first reference fluid, with the sample holder filled with said second reference fluid and finally scanning the sample holder with the porous medium sample therein and saturated with the second reference fluid having the greater x-ray attenuation characteristic.

The present invention further provides an improved method for determining relative permeabilities of porous media and methods for studying the saturation characteristics of a porous medium such as a sample of an earth or rock formation and the like. Those skilled in the art will further appreciate the advantages and superior features of the present invention upon reading the description which follows.

DESCRIPTION OF PREFERRED EMBODIMENTS

Figure 1:
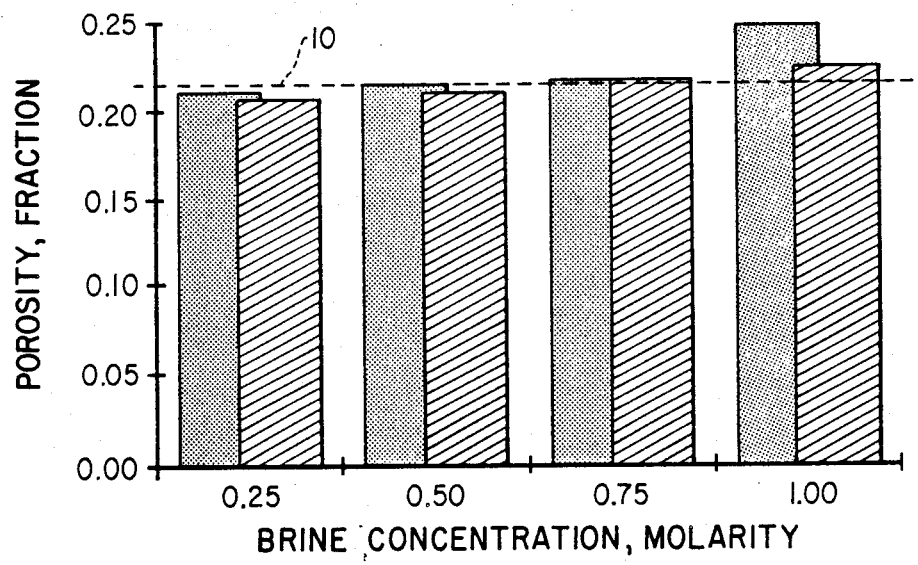

X-ray computed tomography can be considered primarily in four steps including x-ray production wherein an x-ray beam is collimated into a narrow fan shape which defines the plane or "slice" location of the CT image. Data acquisition is obtained through an array of detectors the signal outputs of which can be compared to determined the attenuation of the projected beam. Image reconstruction is carried out by finding the linear attenuation coefficient for all the volume elements along the lines between the source of the x-ray and the detectors. Rotation of the source and detectors during scanning allows for acquisition of projection data along many lines from different directions. Finally, image display by a cathode ray tube, for example, represents the linear attenuation coefficients of the corresponding volume elements in a scanned object. A computer may be used to convert attenuation coefficients into corresponding numerical values such as CT numbers from equation (1). CT numbers may be obtained for various materials and for different x-ray energy levels.

In porosity determination the x-ray linear attenuation coefficient $\mu_{1P}$ of a volume element containing rock matrix material and a single fluid may be expressed as a linear combination of the attenuation from each material:

$$\mu_{1P} = (1-\phi)\mu_r + \phi\mu_f \tag{2}$$

where $\phi$ is the void fraction or porosity of the rock, $\mu_r$ and $\mu_f$ are the x-ray linear attenuation coefficients of the porous media or rock matrix material and the fluid, respectively. By making two attenuation measurements each with a different fluid occupying the pore volume of the porous media sample the following equations are obtained:

$$\mu_{1P}^1 = (1-\phi)\mu_r^1 + \phi\mu_f^1 \tag{3}$$

$$\mu_{1P}{}^2 = (1-\phi)\mu_r{}^2 + \phi\mu_f{}^2 \quad (4)$$

The superscripts 1 and 2 indicate saturation of the porous medium sample with a particular fluid, respectively. Assuming a monoenergetic source, the component of attenuation contributed by the porous media, such as a rock or earth sample is independent of the fluid occupying the pores. Accordingly, these equations may be combined and rearranged to express porosity:

$$\phi = \frac{\mu_{1P}^1 - \mu_{1P}^2}{\mu_f^1 - \mu_f^2} \quad (5)$$

In carrying out the method of the present invention, a commercially available computed tomography scanner may be used such as a type CT9800 scanner manufactured by General Electric Company. This scanner utilizes an x-ray tube which operates at levels of 80, 120, and 140 kilovolts (kV) with currents ranging from 10 to 300 milliamps (mA). The x-ray detector array contains 742 cells approximately 0.04 inches wide filled with xenon gas. The apparatus includes a computer having a central processor and an auxiliary array processor. An operator console contains a video monitor for command/control and another monitor for image display. The apparatus may also be equipped with a graphics workstation such as a type CEMAX 1500X manufactured by CEMAX, Inc., Santa Clara, Calif. to provide color image display and hard copy. This workstation is also adapted to produce high resolution images in two or three dimensions.

Major considerations for performing quantitative CT measurements such as in determining saturation or porosity characteristics of a porous medium, include a provision that the x-ray attenuation of the fluids used in the determination process be distinctly different while occupying the porous medium and that the CT numbers vary linearly with the mixture concentrations. For example, the difference between the CT numbers of oil and water is normally small, in the range of about 200 CT units. This difference may be increased by using certain dopants such as sodium iodide.

A preferred procedure for determining porosity by computed tomography scanning using an apparatus as aforedescribed comprises the steps of (a) obtaining a CT number for a first reference fluid such as air by scanning a suitable sample holder having air only therein. A suitable sample holder may be of a type described in my U.S. Pat. No. 4,710,948, issued Dec. 1, 1987 and assigned to the assignee of this invention. A sample of the porous medium such as a core sample of an earth formation whose porosity is to be determined is saturated with the first reference fluid, such as air, and a CT number is obtained by carrying out step (b) by scanning such a sample saturated with the first reference fluid only. The sample holder is then filled with a second reference fluid which attenuates x-rays to a much greater extent than, for example, air and this second reference fluid is scanned by the CT scanner to complete step (c). The sample of the porous medium is then saturated with the second reference fluid, placed in the sample holder and scanned (step (d)) by the CT scanner to obtain the resulting CT numbers. The CT numbers are proportional to the respective attenuation coefficients, $\mu$, and may be substituted for the coefficients. The resulting CT numbers are then used in place of the respective attenuation coefficients in equation (5) to determine the porosity, $\phi$, of the porous medium. The numerator of equation (5) corresponds to the difference obtained by subtracting the CT number obtained in step (b) from that obtained in step (d). The denominator corresponds to the difference obtained by subtracting the CT number obtained in step (a) from that obtained in step (c). Alternatively, the numerator may be determined by the difference obtained by subtracting the CT number obtained in step (d) from that obtained in step (b), providing the denominator also is determined by subtracting the CT number obtained in step (c) from that obtained in step (a).

The reference fluids used may be liquids or gases, the main requirement being that the two reference fluids attenuate x-rays differently. A liquid reference fluid may be used along with a gas, such as air, and an aqueous solution of sodium iodide. Other suitable water soluble agents include potassium iodide. Two different gases may be used, or the same gas may be used at different pressures to satisfy the requirement of the two reference fluids. Xenon gas, for example, may be used for a first reference fluid at one pressure and again as a second reference fluid at an elevated pressure wherein its x-ray attenuation level is much greater. Oleic phases may also be used. The x-ray attenuation of an oleic phase may be adjusted by addition of an oil soluble dopant such as iododecane.

The method of the present invention may be used to determine both average porosity of a sample as well as local internal porosity. The type of measurement is established by the amount of the sample included in the determination of the CT number. For average sample porosity a region of interest of the sample includes the entire cross section. Whereas local porosity may be determined for any region of interest of a size smaller than the entire cross section. The smallest local porosity measurement may be taken at the limit of resolution of the CT scanning apparatus. Many local porosities may be determined in a cross section to map the porosity variation and three dimensional porosities of both a local or overall type may be determined by the analysis of adjacent "slices" of the sample being analyzed.

EXAMPLE 1

The porosity of a sample of Berea sandstone and a sample of dolomite were analyzed to determine average porosity using the above described method. Porosity sensitivity to different conditions was evaluated using the scanning apparatus above described at power settings at 80 and 120 kV with four concentrations (0.25, 0.50, 0.75, and 1.00 molar) of sodium iodide brine saturating a Berea sandstone and a fine grained dolomite core, respectively. Each of the cores had a 1.50 inch diameter and a length of about 4.0 inches. Reference porosities were determined by the conventional resaturation method. Each of the porous media samples was contained in an aluminum body core holder similar to the core holder described in my above referenced patent. Reference CT numbers were obtained for air by scanning the core holder while "empty". Each liquid sample at the respective concentrations was placed in a low density polyethylene bottle, inserted into the core holder and scanned by the scanning apparatus. The core samples were saturated with the different fluids by submerging them in the respective liquids while under vacuum and were then each scanned in the core holder.

Figure 2:
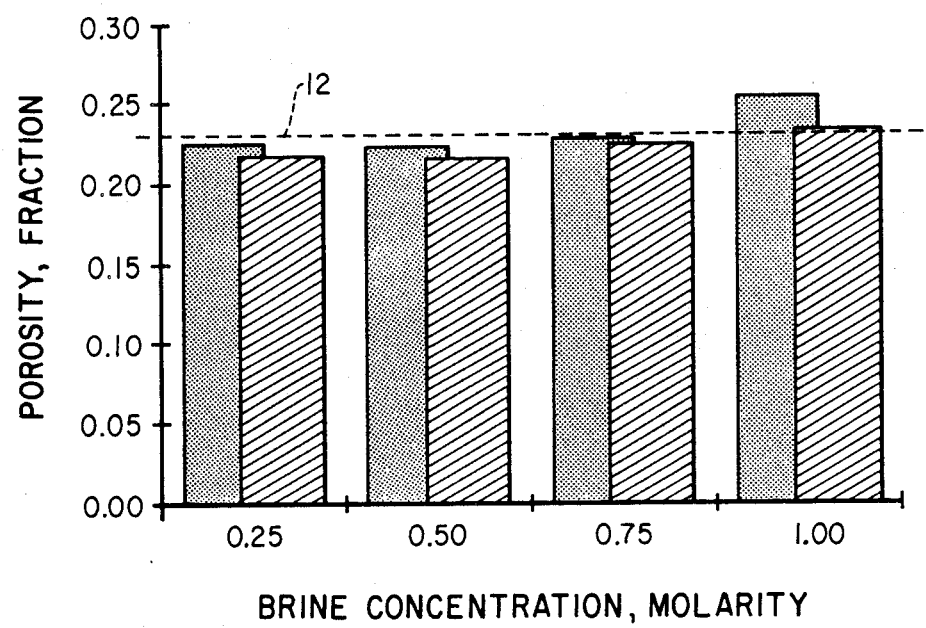

FIGS. 1 and 2 show the average porosities of the Berea sandstone and the dolomite samples, respectively.

For each concentration the bar on the left represents scanning voltage settings of 80 kV and the bar on the right voltage settings of 120 kV. At concentrations of 0.75 molar and less, close agreement (within approximately ±1 porosity percent) is obtained between the CT measured porosities and those determined by the conventional method indicated by dashed lines 10 and 12. With a one molar sodium iodide concentration, the CT number of the brine at 80 kV power setting was at the upper limit of the CT scale and provided the least accurate measurement.

Analyses were performed to estimate the significance of beam hardening on local porosity determination. The procedure determined that the average CT number of a small circular region, approximately 0.3 inches in diameter in the center of a sample and near its periphery. This region is small enough to reflect beam hardening and assumed here as a typical size of interest for local porosity determination. Comparison of apparent porosities at these locations with those determined for the entire cross section of the sample provides an estimate of variations not resulting from actual material heterogeneities. Preliminary scanning provided an initial quantitative check on the underlying assumption of sample uniformity. The analysis was performed for all of the fluid and core sample combinations at both scanning apparatus voltages. The resulting differences (excluding the nonlinear one molar concentrations) between the apparent porosities of the local regions and those based on average sample diameter ranged from a maximum of ±2 porosity percent (80 kV) to less than ±1 porosity percent (120 kV).

Although a preferred embodiment of an improved method for measuring the porosity of porous media such as an earth or rock core samples or the like using x-ray computed tomography, has been described, those skilled in the art will recognize that various substitutions and modifications may be made to the present invention recited in the appended claims without departing from the scope and spirit thereof.

What is claimed is:

1. A method for determining the porosity of a porous medium such as a sample of an earth formation or the like utilizing x-ray computed tomography comprising the steps of:
    providing a sample holder for holding a sample of said porous medium;
    providing an x-ray computed tomography apparatus;
    scanning said sample holder filled with a first fluid to determine a numerical value corresponding to the x-ray linear attenuation coefficient of said first fluid;
    scanning said sample holder with said sample therein saturated with said first fluid to determine a numerical value corresponding to the linear attenuation coefficient of said sample with said first fluid;
    scanning said sample holder filled with a second fluid to determine a numerical value corresponding to the linear attenuation coefficient of said second fluid;
    scanning said sample holder with said sample contained therein and saturated with said second fluid to determine a numerical value corresponding to the linear attenuation coefficient of said sample with said second fluid; and
    comparing the difference of said numerical values corresponding to the linear attenuation coefficients of said sample saturated with said first fluid and said second fluid with the difference between said numerical values corresponding to the linear attenuation coefficients of said first and second fluids to determine the porosity of said sample.

2. The method set forth in claim 1 wherein:
    said first fluid is a gas.

3. The method set forth in claim 1 wherein:
    said second fluid is a liquid.

4. The method set forth in claim 1 wherein:
    said first fluid and second fluid are a gas at different pressure conditions in said sample holder when carrying out the scanning steps for measuring the numerical values corresponding to the linear attenuation coefficients of said first and second fluids and said sample saturated with said first and second fluids, respectively.

5. A method for determining the porosity of a core sample of an earth formation utilizing x-ray computed tomography comprising the steps of:
    providing x-ray computed tomography apparatus;
    measuring the x-ray linear attenuation coefficient of a first fluid with said apparatus;
    measuring the x-ray linear attenuation coefficient of said core sample saturated with said first fluid with said apparatus;
    measuring the x-ray linear attenuation coefficient of a second fluid having a linear attenuation coefficient significantly different from said first fluid with said apparatus;
    measuring the linear attenuation coefficient of said core sample saturated with said second fluid with said apparatus; and
    comparing the difference between the linear attenuation coefficients of said core sample saturated with said first fluid and said second fluid, respectively, with the difference between the linear attenuation coefficients of said first and second fluids, said comparison comprising the basis for determining the porosity of said core sample.

6. A method for determining at least one of the average or localized porosity of a sample of a porous medium such as a sample of an earth formation or the like utilizing x-ray computed tomography comprising the steps of:
    providing a sample holder for holding a sample of said porous medium;
    providing an x-ray computed tomography apparatus;
    scanning said sample holder filled with a first fluid to determine a numerical value corresponding to the x-ray linear attenuation coefficient of said first fluid;
    scanning said sample holder with said sample therein and saturated with said first fluid to determine a numerical value corresponding to the linear attenuation coefficient of said sample with said first fluid;
    scanning said sample holder filled with a second fluid to determine a numerical value corresponding to the linear attenuation coefficient of said second fluid;
    scanning said sample holder with said sample contained therein and saturated with said second fluid to determine a numerical value corresponding to the linear attenuation coefficient of said sample with said second fluid; and calculating the porosity of said sample using the equation:

$$\phi = \frac{\mu_{1P}^1 - \mu_{1P}^2}{\mu_f^1 - \mu_f^2}$$

wherein $\phi$ is porosity and $\mu_{1P}^1$, $\mu_{1P}^2$, $\mu_f^1$ and $\mu_f^2$ comprise numerical values proportional to the linear attenuation coefficients of said sample saturated with said first fluid, said sample saturated with said second fluid, said first fluid and said second fluid, respectively.

7. A method for determining the porosity of a porous medium such as a sample of an earth formation or the like utilizing x-ray computed tomography comprising the steps of:

provinding a sample holder for holding a sample of said porous medium;

providing an x-ray computed tomography apparatus;

scanning said sample holder filled with a first fluid to determine a numerical value corresponding to the x-ray linear attenuation coefficient of said first fluid;

scanning said sample holder with said sample therein saturated with said first fluid to determine a numerical value corresponding to the linear attenuation coefficient of said sample with said first fluid;

scanning said sample holder filled with a second fluid comprising sodium iodide brine having a concentration of sodium iodide of less than about 1.0 molarity, to determine a numerical value corresponding to the linear attenuation coefficient of said second fluid;

scanning said sample holder with said sample contained therein and saturated with said second fluid to determine a numerical value corresponding to the linear attenuation coefficient of said sample with said second fluid; and comparing the difference of said numerical values corresponding to the linear attenuation coefficients of said sample saturated with said first fluid and said second fluid with the difference between said numerical values corresponding to the linear attenuation coefficients of said first and second fluids to determine the porosity of said sample.

* * * * *